United States Patent [19]

Takeda et al.

[11] Patent Number: 4,994,581
[45] Date of Patent: Feb. 19, 1991

[54] PHOSPHORIC ESTERS

[75] Inventors: Motoru Takeda; Mitsuharu Masuda, both of Wakayama; Takashi Imamura, Chiba; Tomihiro Kurosaki, Osaka, all of Japan

[73] Assignee: Kao Corporation, Tokyo, Japan

[21] Appl. No.: 452,419

[22] Filed: Dec. 19, 1989

[30] Foreign Application Priority Data

Dec. 22, 1988 [JP] Japan ................. 63-324650

[51] Int. Cl.$^5$ ........................... C07F 9/06; C07F 9/02
[52] U.S. Cl. .................................. 549/219; 558/179; 558/180; 558/186; 558/188
[58] Field of Search ................ 549/219; 558/179, 180, 558/186, 188

[56]  References Cited

U.S. PATENT DOCUMENTS 4,613,661  9/1986  Lanper et al. .................. 549/219
4,845,239  7/1988  Wakatsuki et al. ............. 549/219

FOREIGN PATENT DOCUMENTS

A242781 10/1987 European Pat. Off. .
2172889 10/1986 United Kingdom .

Primary Examiner—Cecilia Shen
Attorney, Agent, or Firm—Birch, Stewart, Kolasch & Birch

[57]  ABSTRACT

A novel phosphoric ester of the formula (I)

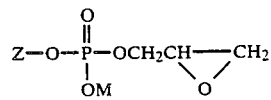

wherein, Z represents the following radicals

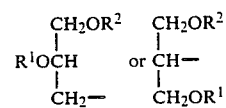

useful as modifiers for amino acids, peptides and proteins which are easily decomposable in living bodies.

8 Claims, 2 Drawing Sheets

PHOSPHORIC ESTERS

BACKGROUND OF THE INVENTION

1. Field of Invention

The present invention relates to novel phosphoric esters and more particularly, to phosphoric esters of the formula (I) and the formula (II)

$$Z-O-\overset{\overset{O}{\|}}{\underset{\underset{OM}{|}}{P}}-OCH_2CH\underset{O}{\overset{}{\diagdown\diagup}}CH_2 \quad (I)$$

wherein Z represents the following radicals $$\begin{array}{cc} CH_2OR^2 & CH_2OR^2 \\ R^1OCH & \text{or} \quad CH- \\ CH_2- & CH_2OR^1 \end{array}$$

wherein $R^1$ and $R^2$ each represent a hydrogen atom, a linear or branched acyl, alkyl or alkenyl group having from 5 to 36 carbon atoms with the proviso that both $R^1$ and $R^2$ are not simultaneously hydrogen atoms; and M represents a hydrogen atom, an alkali metal ion, an alkaline earth metal ion, ammonium, an alkylamine ion or an alkanolamine ion.

$$Z-O-\overset{\overset{O}{\|}}{\underset{\underset{OM}{|}}{P}}-O\underset{}{CH_2}\underset{\underset{OH}{|}}{CH}-\underset{\underset{X}{|}}{CH_2} \quad (II)$$

wherein Z and M have the same meaning defined above, and X represents a halogen atom.

2. Description of the Prior Art

Phosphoric esters are utilized in a wide variety of fields such as in detergents, fabric treating agents, emulsifiers, anticorrosive agents, liquid ion-exchangers or pharmaceutical products, etc.

The present inventors have researched the possibility of widening the usefulness of the phosphoric esters, and have found novel phosphoric esters, a typical one of which is a compound of the formula (III)

$$C_{12}H_{25}-O-\overset{\overset{O}{\|}}{\underset{\underset{OH}{|}}{P}}-OCH_2CH\underset{O}{\overset{}{\diagdown\diagup}}CH_2 \quad (III)$$

having a glycidyl group in a molecule and a process for the preparation thereof (U.S. Pat. No. 4,845,239).

Since the phosphoric esters of the formula (III) have a glycidyl group, they are useful as modifiers of amino acids, peptides or proteins They can be also utilized as monomers having a polymerizable group or modifiers of polymer compounds. Furthermore, they are useful as reagents whereby one can easily synthesize phosphoric esters which have quaternary ammonium groups therein Heretofore, it was difficult to obtain such phosphoric esters commercially.

The phosphoric esters (III) described above have an alkyl group as one substituent As a result, there is no hydrolase which can metabolize it in a living body. Therefore, the phosphoric esters (III) are not biodecomposable, and accumulate in living bodies. The problem described above results in the necessity of developing the enzymatically degradable compounds in living bodies, which are useful for the purposes described above.

SUMMARY OF THE INVENTION

Under these circumstances, the present inventors have made intensive studies and, as a result, found that when a phosphoric ester represented by formula (II) and having a glycerine backbone as a substituent is reacted with a basic compound, the phosphoric diester represented by formula (I) in which a phospholipid is introduced with a glycidyl group, can be readily prepared and that the resulting phosphoric ester (I) and derivatives thereof is easily biodecomposable by an enzyme present in living bodies. The present invention was accomplished based on the above findings.

Accordingly, the present invention is directed to novel phosphoric esters having the formula (I), above. Also, the present invention is directed to novel phosphoric esters of the formula (II) which are intermediates for preparing the phosphoric esters of formula (I).

DETAILED DESCRIPTION OF THE INVENTION AND PREFERRED EMBODIMENTS

Figure 1:
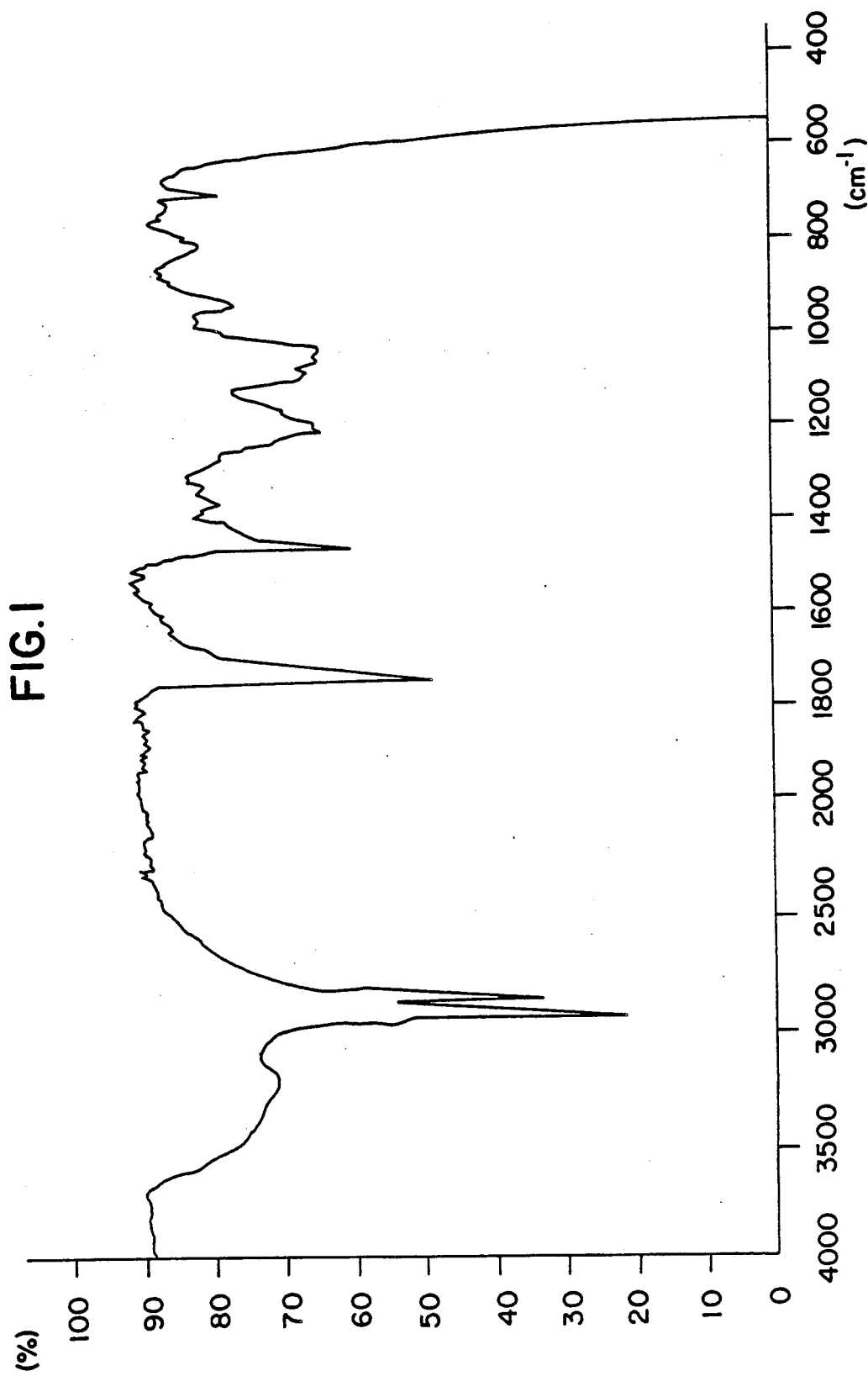
FIG. 1 is the infrared absorption spectrum of dipalmitoyl phosphatidyl monochlorohydrin sodium salt obtained in Example 1.

In the phosphoric esters of formulas (I) and (II) according to the invention, $R^1$ and $R^2$ each represents a linear or branched saturated or unsaturated acyl, a linear or branched alkyl or an alkenyl group having from 5 to 36 carbon atoms. Examples of the acyl group, alkyl group or alkenyl group include valeryl, caproyl, enanthoyl, capryloyl, undecyloyl, lauroyl, tridecanoyl, myristoyl, pentadecanoyl, palmitoyl, heptadecanoyl, staroyl, arachidoyl, behenoyl, pivaloyl, dodecenoyl, docosenoyl, cinnamoyl, isovaleryl, hexcenoyl, dodecenoyl, hexadecenoyl, octadecenoyl, octadecadienoyl, eicosadienoyl, triacontadienoyl, tetradecatrienoyl, hexatrienoyl, octatrienoyl, pentyl, heptyl, hexyl, octyl, nonyl, decyl, dodecyl, tetradecyl, hexadecyl, octadecyl, undecyl, tridecyl, myristyl, pentadecyl, cetyl, heptadecyl, stearyl, arachyl, dococyl, tetracocyl, triacontyl, 2-ethylhexyl, 2-octyldodecyl, 2-undecylhexadecyl, 2-tetradecyloctadecyl, methylheptadecyl, hexenyl, octenyl, decenyl, dodecenyl, hexadecenyl, octadecenyl, tetracocenyl, triacontneyl and the like.

The phosphoric esters of formula (II), which are the intermediates for preparing the phosphoric ester of the formula (I), can be prepared according to the process by the following reaction formula (A)

$$Z-O-\overset{\overset{O}{\|}}{\underset{\underset{OM}{|}}{P}}-OH + X-CH_2CH\underset{O}{\overset{}{\diagdown\diagup}}CH_2 \longrightarrow$$

(IV) \quad\quad (V)

-continued $$Z-O-\underset{\underset{OM}{|}}{\overset{\overset{O}{\|}}{P}}-OCH_2\underset{\underset{OH}{|}}{C}H-\underset{\underset{X}{|}}{C}H_2 \quad (II)$$

wherein Z, M and X have the same meaning defined above.

Namely, the phosphoric esters can be prepared by reacting a glycerophosphatidic acid monoalkali salt (phospholipid) (IV) with a halogen-substituted epoxy compound (V) by any conventional method In the reaction described above, as the glycerophosphatidic mono salt represented by the formula (IV) can be used, glycerophospholipids of the diacyl ester type, monoacyl ester type (lyso type), monoalkenyl ether type (plasmalogen type), monoalkyl ether type, monoalkyl ether monoacyl type, dialkyl ether type, or of the cycloalkylidene type. Phospholipids obtained from natural products using extractive separation and phospholipids synthesized can also be used.

The counter ion of compound (IV) may be an alkali metal such as sodium, potassium, ammonium, alkylamine and alkanolamine. Alkali metals and ammonium are preferred.

The compounds of formula (I) can be used singularly or in admixture. $R^1$ and $R^2$ of formula (I) may be derived from a distribution of natural fatty acid products such as soybean or egg yolk.

The solvents used for the above reaction include chloroform, dichloromethane, methanol, tetrahydrofuran, ethanol and the like or mixtures thereof The reaction temperature used in this reaction process is in the range of from $-30°$ C. to $100°$ C. In order to prevent decomposition of the resultant product, lower temperatures are preferred In this sense, the reaction at a temperature range of from $-10°$ C. to $70°$ C. is preferred.

The halogen-substituted epoxy compounds, which react with phospholipids, include epichlorohydrin, epibromohydrin, epiiodohydrin and the like. They can be used singularly or in admixture.

The amount of halogen-substituted epoxy compound used is in molar excess to compound (IV). In order to raise the yield of the resultant product, it is preferable to use the halogen-substituted epoxy compound (V) in a molar amount of from 2 to 10 times than that of the molar amount of compound (IV).

The phosphoric esters (I) of the invention can be prepared according to the process indicated, for example, by the following reaction formula (B)

$$Z-O-\underset{\underset{OM}{|}}{\overset{\overset{O}{\|}}{P}}-OCH_2\underset{\underset{OH}{|}}{C}H-\underset{\underset{X}{|}}{C}H_2 + \text{basic compound} \longrightarrow$$
(II)

$$Z-O-\underset{\underset{OM}{|}}{\overset{\overset{O}{\|}}{P}}-OCH_2CH\underset{O}{\overset{\diagdown\diagup}{-}}CH_2 + H_2O$$

wherein Z, M and X have the same meaning as defined above provided that when M is a hydrogen atom, one more equivalent of basic compound is necessary in the reaction.

The basic compound may be an alkali metal hydroxide such as sodium hydroxide, potassium hydroxide, etc.

The amount of the basic compound is at least in molar excess to the compound of the formula (II). Accordingly, an equimolar amount or a small excess is usually used, allowing the reaction to proceed quantitatively.

The solvents used for the reaction described above include an appropriate mixture of water, ethanol, methanol or chloroform, etc.

The reaction temperature is in the range of from $-15°$ C. to $40°$ C., preferably at a temperature of from $-10°$ C. to $0°$ C.

In the reaction, although the salt is a byproduct of the reaction, the reaction product may be used, as is, or in the form of the compound of the formula of the invention, depending on the intended purpose The phosphoric esters of the formula (I) and (II) can be also obtained by transphosphatidilation using an enzyme (such as phospholipase D).

The compounds (I) and (II) of the invention obtained by the process described above are generally alkali metal salts. It is possible to exchange the counter ion (salt) or to remove the salt to produce an acid-type phosphoric ester (of the formula (I) and (II), i.e., M=H). The acid-type phosphoric esters can be easily obtained by treating the phosphoric esters(I) or (II) with acidic water after dissolving them into a proper solvent such as chloroform, methanol or water, etc.

Alkaline earth metal salts such as calcium, etc., can be obtained by adding alkaline earth metal chloride, for example, calcium chloride, magnesium chloride into a solution of the acid-type phosphoric ester.

Furthermore, ammonium, alkylamine and alkanolamine salts of the phosphoric esters (I) or (II) can be obtained not only by using ammonium, alkylamine and alkanolamine salt as a starting material, but also by neutralizing the acid-type phosphoric esters (I) or (II) with ammonia water, triethylamine, triethanolamine, etc.

Because the phosphoric esters (I) of the invention have natural basic backbones, amino acids, peptides and protein modified with the phosphoric ester (I) have a good adaptability in living bodies, and are applicable in a wide variety of fields such as in foods, pharmaceuticals, etc. Furthermore, when the phosphoric ester (I) of the invention is reacted, for example, with an amine compound according to the following reaction formula (C), hereinbelow, $$Z-O-\underset{\underset{OM}{|}}{\overset{\overset{O}{\|}}{P}}-OCH_2CH\underset{O}{\overset{\diagdown\diagup}{-}}CH_2 + \underset{\underset{R^5}{|}}{\overset{\overset{R^3}{|}}{N}}-R^4 \longrightarrow$$
(I) \quad (C)

$$Z-O-\underset{\underset{O}{|}}{\overset{\overset{O}{\|}}{P}}-OCH_2\underset{\underset{OH}{|}}{C}H-CH_2-\underset{\underset{R^5}{|}}{\overset{\overset{R^3}{|}}{N}}-R^4$$

a phospholipid having a quaternary ammonium group in the molecule (as will be difficult to obtain industrially in the prior art, i.e. a betaine amphiphilic compound having a phosphoric acid group and ammonium group as the hydrophilic moiety) can be readily obtained, wherein A M and Z have the same meanings defined above; $R^3$, $R^4$ and $R^5$ each represent a hydrogen atom or an organic group.

A variety of phospholipids having various hydrophilic groups can be derived by reacting the phosphoric esters (I) of the invention with other diverse amine compounds or other compounds having active hydrogen atoms.

Because of the polymerizability of the glycidyl radical itself or its reactivity toward a polymer molecule, the phosphoric ester (I) can be utilized as a monomer in the fields of polymer chemistry as a modifier to a polymer compound and as a modifier to a protein.

The present invention is described in detail by way of examples and tests.

The present invention will now be further described by reference to the following illustrative Examples. Of course, the present invention is to be in no way construed as being limited by these Examples.

EXAMPLE 1

Preparation of dipalmitoyl phosphatidyl monochlorohydrin (the compound of formula (II), wherein $R^1=R^2=$ palmitoyl, X=chlorine, M=sodium): 333 mg (0.5 mmol) of mono sodium dipalmitoyl phosphatidate (purity is greater than 98%, obtained by purifying a product produced by SIGMA Corp. refer to "DPPA-Na" below), 300 ml of chloroform and 105 ml of methanol was charged into 1 - four necked flask equipped with a stirrer, thermometer, condenser and dropping funnel (refer to "reactor" below), and were agitated to obtain a uniform solution. The solution was heated up to reflux temperature under nitrogen atmosphere, and 245 mg (2.75 mmol) of epichlorohydrin was added to the solution. The progress of the reaction was followed by thin layer chromatography (TLC), while stirring was continued under reflux temperature. After confirming a disappearance of DPPA-Na the reaction was ended. The reaction mixture was concentrated, and the products were separated by using preparative TLC (silica gel, eluent; a mixture of chloroform: methanol 25% ammonia water: water 50:20:2:1). 210 mg (yield 57.5%) of dipalmitoyl phosphatidyl monochlorohydrin mono sodium salt was obtained by collecting that portion having an Rf=0.68.

The product was identified as dipalmitoyl phosphatidyl monochlorohydrin by NMR analysis, IR and elemental analysis. The data is shown as follows $^1$H-NMR (270 MHz): ($CDCl_3:CD_3OD=2:1$. TMS standard ppm) 0.82 (t. 6H. the methyl in palmitoyl group (hereinafter PA) 1.25 (s. 56H. methylene in PA) 1.54 (m. 4H. carbonyl β-methylene in PA) 2.25 (m. 4H. carbonyl -methylene in PA) 3.52 (m. 3H. $POCH_2(OH)$. $CH_2CH(OH)CH_2Cl$) 3.80 (m. 2H. $PO\overline{CH_2}(OH)$. $CH_2CH(OH)\overline{CH_2}Cl$) 3.96 (m. 2H. 1-methylene in phosphatidyl group (hereinafter PH)) 4.18 (m. 1H. 3-methylene in PH) 4.40 (m. 1H. 3-methylene in PH) 5.23 (m. 1H. 2-methylene in PH)

|  | Elemental analysis: | | | |
|---|---|---|---|---|
|  | C (%) | H (%) | P (%) | O (%) |
| Calculated | 61.64 | 9.94 | 4.18 | 4.79 |
| Found | 61.91 | 9.85 | 4.32 | 4.44 |

IR Spectrum (see FIG. 1):
3300 cm$^1$ (PO—H)
2950. 2880 cm$^{-1}$ (C—H)
1760 cm$^{-1}$ (C=O)
1492 cm$^{-1}$ (C—H)
1240 cm$^{-1}$ (P=O)
1120-1050 cm$^{-1}$ (C-O—P—O)

EXAMPLE 2

Preparation of dipalmitoyl phosphatidyl propenol oxide (the compound of formula (I), wherein $R^1=R^2=$ palmitoyl, and M=sodium):

200 mg (0.266 mmol) of dipalmitoyl phosphatidyl monochlorohydrin, which was prepared in Example 1. 200 ml of chloroform and 50 ml where charged into a reactor, and were agitated to obtain a uniform solution Thereafter, the solution was cooled to a temperature in the range of −10° C. to 0° C., to which was gradually added an aqueous solution of sodium hydroxide (0.266 mmol), followed by agitation for 30 minutes. The reaction mixture was evaporated under reduced pressure to remove the solvent, and the products were separated by using preparative TLC (silica gel, eluent; chloroform: methanol: 25% ammonia water: water=50:20:2:1). 210 mg (yield 76%) of dipalmitoyl phosphatidyl propenoloxide was obtained by collecting that portion having an Rf=0.51.

The product was identified as dipalmitoyl phosphatidyl propenoloxide by NMR analysis, IR and elemental analysis The data is shown as follows $^1$H-NMR (270 MHz): ($CDCl_3:CD_3OD=2:1$. TMS standard ppm): 0.82 (t. 6H. the methyl in palmitoyl group (hereinafter PA)) 1.25 (s. 56H. methylene in PA) 1.54 (m. 4H. carbonyl β-methylene in PA) 2.25 (m. 4H. carbonyl -methylene in PA) 2.75 (m. 1H. end methylene in glycidyl group) 2.84 (m. 1H. end methylene in glycidyl group) 3.25 (broad 1H. methylene in glycidyl group) 3.6–4.0 (m. 4H. $CH_2OPOCH_2$) 3.96 (m. 2H. 1-methylene in phosphatidyl group (hereinafter PH)) 4.18 (m. 1H. 3-methylene in PH) 4.40 (m. 1H. 3-methylene in PH) 5.23 (m. 1H. 2-methylene in PH)

|  | Elemental analysis: | | |
|---|---|---|---|
|  | C (%) | H (%) | P (%) |
| Calculated | 64.83 | 10.31 | 4.41 |
| Found | 64.66 | 10.60 | 4.12 |

Figure 2:
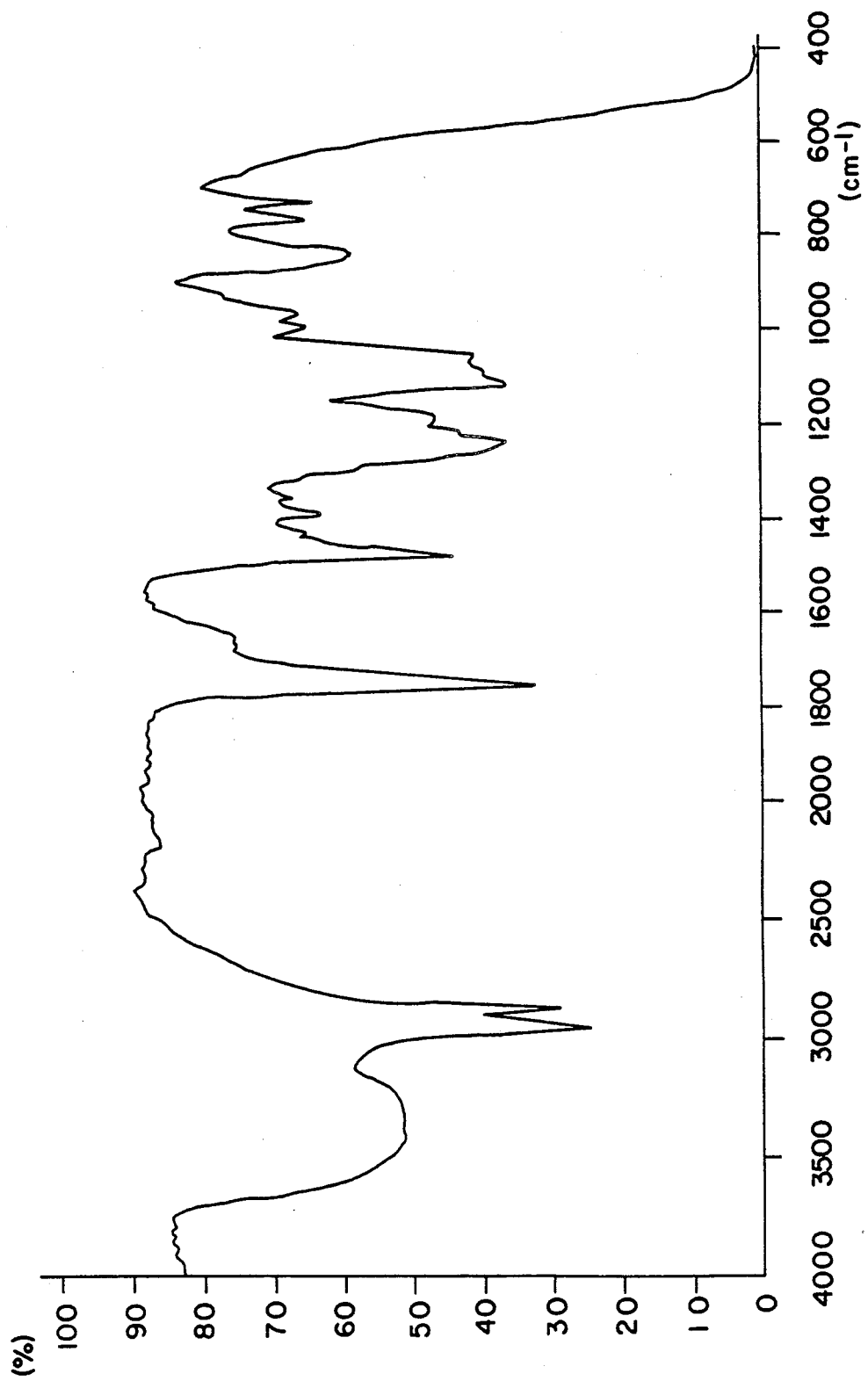
FIG. 2 is the infrared absorption spectrum of dipalmitoyl phosphatidyl propenol oxide sodium salt obtained in Example 2.

IR Spectrum (see FIG. 2):
3300 cm$^{-1}$ (PO—H)
2950. 2880 cm$^{-1}$ (C—H)
1760 cm$^{-1}$ (C=O)
1492 cm$^{-1}$ (C—H)
1240 cm$^{-1}$ (P=O)
1120-1050 cm$^{-1}$ (C—O—P—O)

EXAMPLE 3

Preparation of soybean phosphatidyl monochlorohydrin and soybean phosphatidyl propenoloxide:

(i) 300 mg (0.5 mmol) of mono sodium soybean phosphatidate (which was obtained by hydrolizing a phospholipid extracted from soybean with the enzyme PHOSHOLIPASE-D), hereinafter soybean PA-Na below), 300 ml of chloroform and 150 ml of methanol were charged into a reactor, and were agitated to obtain a uniform solution The solution was heated up to reflux temperature under nitrogen atmosphere, and 254 mg (2.75 mmol) of epichlorohydrin was added into the solution The progress of the reaction was followed by thin layer chromatography (TLC), while stirring was continued under reflux temperature. After confirming a disappearance of the starting material soybean PA-Na, the reaction was ended. The reaction mixture was concentrated, and the products were separated by using preparative TLC (silica gel, eluent; chloroform: methanol: 25% ammonia water: water=50:20:2:1). 190 mg of soybean phosphatidyl monochlorohydrin mono sodium salt was obtained by collecting that portion having an Rf=0.72-0.64.

(ii) Soybean phosphatidyl monochlorohydrin mono sodium salt prepared above, 200 ml of chloroform and 50 ml of ethanol were charged into a reactor, and were agitated to obtain a uniform solution Thereafter, the solution was cooled to a temperature in the range of −10° C. to 0° C., to which was gradually added an aqueous solution of sodium hydroxide (equal molar to said phosphatidyl compound), followed by agitation for 30 minutes. The reaction mixture was evaporated under reduced pressure to remove the solvent, and was separated by using preparative TLC (silica gel, eluent; chloroform: methanol 25% ammonia water: water=50:20:2:1). 82 mg of soybean phosphatidyl propenoloxide sodium salt was obtained by collecting that portion having an Rf=0.55-0.49.

The product was identified as soybean phosphatidyl propenoloxide sodium salt by NMR analysis $^1$H-NMR (270 MHz) (CDCl$_3$:CD$_3$OD=2:1. TMS standard ppm) 0.82 (t. 6H. methyl in fatty acid moiety (hereinafter FA)) 1.25 (s. 54H. methylene in FA) 1.54 (m. 4H. carbonyl β-methylene in FA) 2.05 (M. 2.2h. olefinic methylene in FA) 2.25 (m. 4H. carbonyl -methylene in FA) 2.75-2.95 (m. 6.2H. end methylene in glycidyl group. methylene between olefinic bond in FA) 3.25 (broad 1H. methylene in glycidyl group) 3.6-4.0 (m. 4H. CH$_2$OPOCH$_2$) 3.96 (m. 2H. 1-methylene in phosphatidyl group (hereinafter PH)) 4.18 (m. 1H. 3-methylene in PH) 4.40 (m. 1H. 3-methylene in PH) 5.23 (m. 1H. 2-methylene in PH) 5.33 (m. 6.3H. olefin in FA)

EXAMPLE 4

Preparation of 1-decanoyl-2-pentanoylglycero-3-phosphopropenoloxide potassium salt (the compound of formula (I), wherein R$^1$=decanoyl, R$^2$=pentanoyl and M=potassium):

(i) 300 mg (0.695 mmol) of mono potassium 1-decanoyl-2-pentanoylglycero-3-phosphate, 300 ml of chloroform and 150 ml of methanol were charged into a reactor, and were agitated to obtain a uniform solution The solution was heated up to reflux temperature under nitrogen atmosphere, and 275 mg (2.79 mmol) of epichlorohydrin was added into the solution The progress of the reaction was followed by thin layer chromatography (TLC), while stirring was continued under reflux temperature. After confirming a disappearance of mono potassium 1-decanoyl-2-pentanoylglycero-3-phosphate, the reaction was ended. The reaction mixture was concentrated, and was separated by using preparative TLC (silica gel, eluent; chloroform: methanol: 25% ammonia water: water=50:22:2:1). 212 mg of 1-decanoyl-2-pentanoylglycero-3-phosphomonochlorohydrin mono potassium salt was obtained by collecting the portion having an Rf=0.49-0 43.

(ii) 1-decanoyl-2-pentanoylglycero-3-phosphomonochlorohydrin mono potassium salt prepared above, 200 ml of chloroform and 50 ml of ethanol were charged into a reactor, and were agitated to obtain a uniform solution. Thereafter, the solution was cooled to a temperature in the range of −10° C. to 0° C., to which was gradually added an aqueous solution of sodium hydroxide in an amount equal molar to said phosphatidyl compound, followed by agitation for 30 minutes. The reaction mixture was evaporated under reduced pressure to remove the solvent, and was separated by using preparative TLC (silica gel, eluent; chloroform: methanol 25% ammonia water: water=50:22:2:1). 130 mg (yield 39.5%, based upon phosphatidate as starting material, hereinafter same meaning) of 1-decanoyl-2-pentanoylglycero-3-phosphatidylpropenoloxide mono potassium salt was obtained by collection that portion having an Rf=0.55-0.49.

|  | Elemental analysis: | | |
|---|---|---|---|
|  | C (%) | H (%) | P (%) |
| Calculated | 49.99 | 7.59 | 6.14 |
| Found | 49.86 | 7.84 | 5.99 |

EXAMPLE 5

Preparation of dioctadecenoylglycero-3phosphopropenoloxide monoethanolamine salt (the compound of formula (I), wherein R$^1$=r$^2$=octadecenoyl, and M=monoethanolamine)

(i) 300 mg (0.357 mmol) of monoethanolammonium dioctadecenoylglycero-3-phosphate, 300 ml of chloroform and 150 ml of methanol were charged into a reactor, and were agitated to obtain a uniform solution. The solution was heated up to reflux temperature under nitrogen atmosphere, and 169 mg (1.83 mmol) of epichlorohydrin was added into the solution The progress of the reaction was followed by thin layer chromatography (TLC), while stirring was continued under reflux temperature. After confirming the disappearance of monoethanolammonium dioctadecenoylglycero-3-phosphate, the reaction was ended. The reaction mixture was concentrated, and was separated by using preparative TLC (silica gel, eluent; chloroform: methanol: 25% ammonia water: water=50:20:2:1). 171 mg (yield 52.2%) of dioctadecenoylglycero-3-phosphomonochlorohydrin monoethanolamine salt was obtained by collecting that portion having an Rf=0.49-0.43.

(ii) Dioctadecenoylglycero-3-phosphomonochlorohydrin monoethanolamine salt prepared above, 200 ml of chloroform and 50 ml of ethanol were charged into a reactor, and were agitated to obtain a uniform solution Thereafter, the solution was cooled to a temperature in the range of −10° C. to 0° C., to which was gradually added an aqueous solution of sodium hydroxide equal molar to said phosphatidyl compound, followed by agitation for 30 minutes. The reaction mixture was evaporated under reduced pressure to remove the solvent, and the products were separated by using preparative TLC (silica gel, eluent; chloroform: methanol: 25% ammonia water: water .=50:20:2:1). 60 mg (yield 19%) of dioctadecenoylglycero-3-phosphatidylpropenoloxide mono monoethanolamine salt was obtained by collecting that portion having an Rf=0.40-0.37.

| | Elemental analysis: | | |
|---|---|---|---|
| | C (%) | H (%) | P (%) |
| Calculated | 62.70 | 10.41 | 3.51 |
| Found | 62.55 | 10.30 | 3.31 |

EXAMPLE 6

Preparation of ditriacontenoylglycero-2phosphopropenoloxide mono sodium salt (the compound of formula (I), wherein $R^1=R^2=$ triacontenoyl and M=sodium)

(i) 300 mg (0.278 mml) of mono sodium triacontenoylglycero-2-phosphate, 300 ml of chloroform and 150 ml of methanol were charged into a reactor, and were agitated to obtain a uniform solution The solution was heated up to reflux temperature under nitrogen atmosphere, and 131 mg (1.42 mmol) of epichlorohydrin was added into the solution. The progress of the reaction was followed by thin layer chromatography (TLC), while stirring was continued under reflux temperature. After confirming a disappearance of mono sodium triacontenoylglycero-2-phosphate, the reaction was ended. The reaction mixture was concentrated, and the products were separated by using preparative TLC (silica gel, eluent; chloroform: methanol: 25% ammonia water: water=50:20:2:1:). 155 mg (yield 48.2%) of ditriacontenoylglycero-2-phosphomonochlorohydrin mono sodium salt was obtained by collecting that portion having an Rf=0.65.

(ii) Ditriacontenoylglycero-2-phosphomonochlorohydrin mono sodium salt prepared above, 200 ml of chloroform and 50 ml of ethanol were charged into a reactor, and were agitated to obtain a uniform solution. Thereafter, the solution was cooled to a temperature in the range of $-10°$ C. to $0°$ C., to which was gradually added an aqueous solution of sodium hydroxide equal molar to said phosphatidyl compound, followed by agitation for 30 minutes. The reaction mixture was evaporated under reduced pressure to remove a solvent, and the products were separated by using preparative TLC (silica gel, eluent; chloroform: methanol 25% ammonia water: water =50:20:2:1). 127 mg (yield 51.8%) of ditriacontenoylglycero-2-phosphopropenoloxidemonosodium salt was obtained by collecting that portion having an Rf=0.54.

| | Elemental Analysis: | | |
|---|---|---|---|
| | C (%) | H (%) | P (%) |
| Calculated | 70.80 | 11.52 | 2.77 |
| Found | 70.86 | 11.82 | 2.66 |

EXAMPLE 7

Preparation of dioctadecylglycero-3phosphopropenoloxide mono sodium salt (the compound of formula (I), $R^1=R^2=$ octadecyl and M=sodium)

(i) 250 mg (0.351 mmol) of mono sodium dioctadecylglycero-3-phosphate, 300 ml of chloroform and 150 ml of methanol were charged into a reactor, and were agitated to obtain a uniform solution.

The solution was heated up to reflux temperature under nitrogen atmosphere, and 166 mg 1.79 mmol) of epichlorohydrin was added into the solution. The progress of reaction was followed by thin layer chromatography (TLC), while stirring was continued under reflux temperature. After confirming the disappearance of mono sodium dioctadecylglycero-3-phosphate, the reaction was ended. The reaction mixture was concentrated, and the products were separated by using preparative TLC (silica gel, eluent: chloroform: methanol: 25% ammonia water: water=50:20:2:1:). 139 mg (yield 50.0%) of dioctadecylglycero-3-phosphomonochlorohydrin sodium salt was obtained by collecting the portion having an Rf=0.70.

(ii) Dioctadecylglycero-3-phosphomonochlorohydrin sodium salt prepared above, 200 ml of chloroform and 50 ml of ethanol were changed into a reactor, and were agitated to obtain a uniform solution Thereafter, the solution was cooled to a temperature in the range of $-10°$ C. to $0°$ C., to which was gradually added an aqueous solution of sodium hydroxide in an amount equal molar to said phosphatidyl compound, followed by agitation for 30 minutes. The reaction mixture was evaporated under reduced pressure to remove a solvent, and was purified by using preparative TLC (silica gel, eluent; chloroform: methanol: 25% ammonia water: water=50:20:2:1). 81 mg (yield 30.7%) of dioctadecylglycero-3phosphopropenoloxide sodium salt was obtained by collecting that portion having an Rf=0.54.

| | Elemental Analysis: | | |
|---|---|---|---|
| | C (%) | H (%) | P (%) |
| Calculated | 66.81 | 11.21 | 4.10 |
| Found | 67.00 | 11.25 | 3.85 |

Test

Decomposition test with enzyme

Soybean phosphatidyl monochlorohydrin sodium salt and soybean phosphatidylpropenoloxide sodium salt were dissolved respectively in chloroform. To the solution obtained above a phosphoric buffer solution (PH7, calcium ion content of 250 mM) containing phospholipase $A_2$ (SIGMA Corp.) was added, and stirred at $40°$ C. for 6 hours After stirring, the disappearance of the starting materials was confirmed by TLC. The decomposition rate of each material was 100%.

What is claimed is:

1. A phosphoric ester of the formula (I):

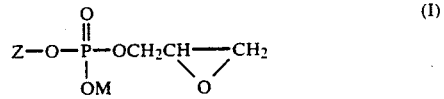

wherein Z represents the following radicals

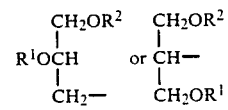

wherein $R^1$ and $R^2$ each represent a hydrogen atom, an acyl group which is residue of a linear or branched aliphatic carboxylic acid having 5 to 36 carbon atoms, a linear or branched alkyl group having 5 to 36 carbon atoms or a linear or branched alkenyl group having from 5 to 36 carbon atoms with the proviso that both $R^1$ and $R^2$ are not simultaneously hydrogen atoms; and M represents a hydrogen atom, an alkali metal ion, and alkaline earth metal ion, ammonium, an alkylamine ion or an alkanolamine ion.

2. The phosphoric ester of claim 1, wherein said acyl group is selected from the group consisting of valeryl, caproyl, enanthoyl, capryloyl, undecyloyl, lauroyl, tridecanoyl, myristoyl, pentadecanoyl, palmitoyl, heptadecanoyl, stearoyl, arachidoyl, behenoyl, pivaloyl, dodecenoyl, docosenoyl, cinnamoyl, isovaleryl, hexcenoyl, dodecenoyl, hexadecenoyl, octadecenoyl, octadecadienoyl, eicosadienoyl, triacontadienoyl, tetradecatrienoyl, hexatrienoyl and octatrienoyl.

3. The phosphoric ester of claim 1, wherein said alkyl group is selected from the group consisting of pentyl, heptyl, hexyl, octyl, nonyl, decyl, dodecyl, tetradecyl, hexadecyl, octadecyl, undecyl, tridecyl, nyristyl, pentadecyl, cetyl, heptadecyl, stearyl, arachyl, dococyl, tetracocyl, triacontyl, 2-ethylhexyl; 2-octyldodecyl, 2-undecylhexadecyl, 2-tetradecyloctadecyl and methylheptadecyl.

4. The phosphoric ester of claim 1, wherein said alkenyl group is selected from the group consisting of hexenyl, octenyl, decenyl, dodecenyl, hexadecenyl, octadecenyl, tetracocenyl and triacontenyl.

5. A phosphoric ester of the formula (II):

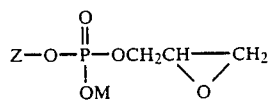
(II)

wherein Z represents the following radicals

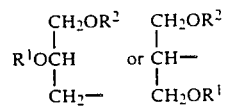

wherein R¹ and R² each represent a hydrogen atom, an acyl group which is residue of a linear or branched aliphatic carboxylic acid having 5 to 36 carbon atoms, a linear or branched alkyl group having 5 to 36 carbon atoms or a linear or branched alkenyl group having from 5 to 36 carbon atoms with the proviso that both R¹ and R² are not simultaneously hydrogen atoms; and M represents a hydrogen atom, an alkali metal ion, an alkaline earth metal ion, ammonium, an alkylamine ion or an alkanolamine ion.

6. The phosphoric ester of claim 5, wherein said acyl group is selected from the group consisting of valeryl, caproyl, enanthoyl, capryloyl, undecyloyl, lauroyl, tridecanoyl, myristoyl, pentadecanoyl, palmitoyl, heptadecanoyl, stearoyl, arachidoyl, behenoyl, pivaloyl, dodecenoyl, docosenoyl, cinnamoyl, isovaleryl, hexcenoyl, dodecenoyl, hexadecenoyl, octadecenoyl, octadecadienoyl, eicosadienoyl, triacontadienoyl, tetradecatrienoyl, hexatrienoyl and octatrienoyl.

7. The phosphoric ester of claim 5, wherein said alkyl group is selected from the group consisting of pentyl, heptyl, hexyl, octyl, nonyl, decyl, dodecyl, tetradecyl, hexadecyl, octadecyl, undecyl, tridecyl, nyristyl, pentadecyl, cetyl, heptadecyl, stearyl, arachyl, dococyl, tetracocyl, triacontyl, 2-ethylhexyl, 2-ocytyldodecyl, 2-undecylhexadecyl, 2-tetradecyloctadecyl and methylheptadecyl.

8. The phosphoric ester of claim 5, wherein said alkenyl group is selected from the group consisting of hexenyl, octenyl, decenyl, dodecenyl, hexadecenyl, octadecenyl, tetracocenyl and triacontenyl.

* * * * *